(12) United States Patent
Sosne et al.

(10) Patent No.: US 8,399,412 B2
(45) Date of Patent: Mar. 19, 2013

(54) METHOD OF TREATING OR PREVENTING TISSUE DETERIORATION, INJURY OR DAMAGE DUE TO PERIODONTAL DISEASE OR DISEASE OF ORAL MUCOSA, AND/OR DOWNREGULATING NF-KAPPABETA OR SUPRESSING NF-KAPPABETA-MEDIATED ACTIONS

(75) Inventors: Gabriel Sosne, Oak Park, MI (US); Michelle Wheater, Warren, MI (US); Allan L. Goldstein, Washington, DC (US)

(73) Assignee: RegeneRx Biopharmaceuticals, Inc., Rockville, MD (US)

( * ) Notice: Subject to any disclaimer, the term of this patent is extended or adjusted under 35 U.S.C. 154(b) by 727 days.

(21) Appl. No.: 12/444,331

(22) PCT Filed: Oct. 5, 2007

(86) PCT No.: PCT/US2007/021435
§ 371 (c)(1), (2), (4) Date: Apr. 3, 2009

(87) PCT Pub. No.: WO2008/045345
PCT Pub. Date: Apr. 17, 2008

(65) Prior Publication Data
US 2010/0048474 A1 Feb. 25, 2010

Related U.S. Application Data
(60) Provisional application No. 60/849,841, filed on Oct. 6, 2006, provisional application No. 60/851,992, filed on Oct. 17, 2006, provisional application No. 60/859,521, filed on Nov. 17, 2006, provisional application No. 60/878,701, filed on Jan. 5, 2007.

(51) Int. Cl.
*A61K 38/17* (2006.01)
(52) U.S. Cl. .......................... 514/16.6; 514/12
(58) Field of Classification Search ........................ None
See application file for complete search history.

(56) References Cited

FOREIGN PATENT DOCUMENTS

| | | | |
|---|---|---|---|
| WO | 0006190 | | 2/2000 |
| WO | WO 00/06190 | * | 2/2000 |
| WO | WO 03/020215 | * | 3/2003 |
| WO | 2004/035008 A2 | | 4/2004 |

OTHER PUBLICATIONS

A. Goldstein et al. "Thymosin β4: actin-sequestering protein moonlights to repair injured tissues," Trends in Molecular Medicine, vol. 11, No. 9, Sep. 2005, pp. 421-429.
W. Loesche et al.: "Periodontal Disease as a Specific, albeit Chronic, Infection: Diagnosis and Treatment," Clinical Microbiology Review, vol. 14, No. 4, Oct. 2001, pp. 727-752.
Supplementary European Search Report and European Search Opinion issued in corresponding European Application No. 07839306.3-2107, dated May 3, 2011, 6 pages.

* cited by examiner

*Primary Examiner* — Christopher R. Tate
*Assistant Examiner* — Roy Teller
(74) *Attorney, Agent, or Firm* — Rothwell, Figg, Ernst & Manbeck, P.C.

(57) ABSTRACT

A method of treatment for treating, at least partly preventing, inhibiting or reducing tissue deterioration, injury or damage due to a periodontal disease or disease of oral mucosa, or for restoring tissue adversely affected by the disease, in a subject, and/or for downregulating NF-kappaB or suppressing NF-kappaB mediated action in a body, organ, tissue or cell, includes administering to a subject, body, organ, tissue or cell an effective amount of a composition including a peptide agent including at least one of Thymosin beta 4 (Tβ4), an isoform of Tβ4, an N-terminal fragment of Tβ4, a C-terminal fragment of Tβ4, Tβ4 sulfoxide, an LKKTET peptide or conservative variant thereof, an LKKTNT peptide or conservative variant thereof, a KLKKTET peptide or conservative variant thereof, an LKKTETQ peptide or conservative variant thereof, Tβ4$^{ala}$, Tβ9, Tβ10, Tβ11, Tβ12, Tβ13, Tβ14, Tβ15, gelsolin, vitamin D binding protein (DBP), profilin, cofilin, depactin, DnaseI, vilin, fragmin, severin, capping protein, β-actinin, acumentin, an actin-sequestering peptide, an actin binding peptide, an actin-mobilizing peptide, an actin polymerization-modulating peptide, or a stimulating agent that stimulates production of an effective amount of the peptide agent in the subject, body, organ, tissue or cell.

10 Claims, 7 Drawing Sheets

METHOD OF TREATING OR PREVENTING TISSUE DETERIORATION, INJURY OR DAMAGE DUE TO PERIODONTAL DISEASE OR DISEASE OF ORAL MUCOSA, AND/OR DOWNREGULATING NF-KAPPABETA OR SUPRESSING NF-KAPPABETA-MEDIATED ACTIONS

CROSS REFERENCE TO RELATED APPLICATION(S)

This application is a 35 U.S.C. §371 National Phase Entry Application from PCT/US2007/021435, filed Oct. 5, 2007, and designating the United States. This application also claims the benefit of U.S. Provisional Application Nos. 60/849,841, filed Oct. 6, 2006, 60/851,992, filed Oct. 17, 2006, 60/859,521, filed Nov. 17, 2006, and 60/878,701, filed Jan. 5, 2007, each of which is incorporated by reference in their entirety.

CROSS-REFERENCE OF RELATED APPLICATIONS

The present application is a non-provisional and claims benefit of U.S. Provisional Application No. 60/849,841, filed Oct. 6, 2006. The present application also claims the benefit of U.S. Provisional Application No. 60/851,992, filed Oct. 17, 2006, U.S. Provisional Application No. 60/859,521, filed Nov. 17, 2006, and U.S. Provisional Application No. 60/878,701, filed Jan. 5, 2007, all of which are incorporated herein in their entirety.

The Sequence Listing was created on Aug. 6, 2012, as file name 2600-205_st25.txt, which is 2 kb. The Sequence Listing is hereby incorporated by reference into the present application.

BACKGROUND OF THE INVENTION

1. Field of the Invention

The present invention relates to the field of treating or preventing tissue deterioration, injury or damage due to periodontal disease or disease of oral mucosa, and/or downregulating or suppressing NF-kappaB-mediated actions in a body.

2. Description of the Background Art

NF-kappaB is the prototype of a family of dimeric transcription factors made from monomers that have approximately 300 amino-acid Rel regions which bind to DNA, interact with each other, and bind the I kappaB inhibitors. Activation of NF-kappaB to move into the nucleus is controlled by the targeted phosphorylation and subsequent degradation of I kappaB. There are multiple forms of I kappa B that appear to regulate NF-kappaB by distinct mechanisms. NF-kappaB can be activated by exposure of cells to LPS or inflammatory cytokines such as TNF or IL-1, viral infection or expression of certain viral gene products, UV irradiation, B or T cell activation, and by other physiological and nonphysiological stimuli. NF-kappaB activation has been implicated in many biological processes, including inflammation, immunoregulation, apoptosis, neuronal function, cell growth and transportation, and cell proliferation.

Inflammatory responses are a major component of secondary injury and play a central role in mediating the pathogenesis of acute and chronic spinal cord injury (SCI). The nuclear factor-kappaB (NF-kappaB) family of transcription factors is required for the transcriptional activation of a variety of genes regulating inflammatory, proliferative, and cell death responses of cells. NF-kappaB activation occurs as early as 0.5 hr postinjury and persists for at least 72 hr. Activated NF-kappaB has been detected in macrophages/microglia, endothelial cells, and neurons within the injured spinal cord. Colocalization of activated NF-kappaB with the NF-kappaB-dependent gene product, inducible nitric oxide synthase (iNOS), suggests functional implications for this transcription factor in the pathogenesis of acute spinal cord injury.

Periodontal (gum) diseases, including gingivitis and periodontitis, are serious infections that, left untreated, can lead to tooth loss. Periodontal disease can result from chronic bacterial infection that affects the gums and bone supporting the teeth.

Periodontal disease can affect one tooth or many teeth. It often begins when the bacteria in plaque causes the gums to become inflamed.

Gingivitis is the mildest form of periodontal disease. It causes the gums to become red, swollen, and bleed easily. There is usually little or no discomfort at this stage.

Untreated gingivitis can advance to periodontitis. With time, plaque can spread and grow below the gum line. Toxins produced by the bacteria in plaque irritate the gums. The toxins stimulate a chronic inflammatory response in which the body in essence turns on itself, and the tissues and bone that support the teeth are broken down and destroyed. Gums separate from the teeth, forming pockets (spaces between the teeth and gums) that become infected. As the disease progresses, the pockets deepen and more gum tissue and bone are destroyed. Often, this destructive process has very mild symptoms. Eventually, teeth can become loose and may have to be removed.

Periodontitis as a Manifestation of Systemic Diseases are forms of periodontal disease which often begin at a young age, associated with one of several systemic diseases, such as diabetes.

Necrotizing Periodontal Diseases are forms of periodontal disease which are infections characterized by necrosis of gingival tissues, periodontal ligament and alveolar bone. These lesions are most commonly observed in individuals with systemic conditions including, but not limited to, HIV infection, malnutrition and immunosuppression.

Aggressive Periodontitis is a form of periodontitis that occurs in patients who are otherwise clinically healthy. Common features include rapid attachment loss and bone destruction and familial aggregation.

Chronic Periodontitis is a form of periodontal disease resulting in inflammation within the supporting tissues of the teeth, progressive attachment and bone loss and is characterized by pocket formation and/or recession of the gingiva. It is recognized as the most frequently occurring form of periodontitis. It is prevalent in adults, but can occur at any age. Progression of attachment loss usually occurs slowly, but periods of rapid progression can occur.

Up to 30% of the population may be genetically susceptible to gum disease. Despite aggressive oral care habits, these people may be six times more likely to develop periodontal disease.

There remains a need in the art for methods of treatment for treating, preventing, inhibiting or reducing tissue deterioration, injury or damage due to periodontal disease or disease of oral mucosa and/or influencing activities of NF-kappaB in a body.

SUMMARY OF THE INVENTION

In accordance with one aspect, a method of treatment for at least one of treating, at least partly preventing, inhibiting or reducing tissue deterioration, injury or damage due to a periodontal disease or disease of oral mucosa, and/or for restoring tissue adversely affected by said disease, in a subject, and/or for downregulating NF-kappaB or suppressing NF-kappaB-mediated action in a body, organ, tissue or cell, comprises administering to a subject, body, organ, tissue or cell an effective amount of a composition comprising a peptide agent comprising at least one of Thymosin beta 4 (Tβ4), an isoform of Tβ4, an N-terminal fragment of Tβ4, a C-terminal fragment of Tβ4, Tβ4 sulfoxide, an LKKTET (SEQ ID NO.: 1) peptide or conservative variant thereof, an LKKTNT (SEQ ID NO.: 2) peptide or conservative variant thereof, a KLKKTET (SEQ ID NO.: 3) peptide or conservative variant thereof, an LKKTETQ (SEQ ID NO.: 4) peptide or conservative variant thereof, Tβ4$^{ala}$, Tβ9, Tβ10, Tβ11, Tβ12, Tβ13, Tβ14, Tβ15, gelsolin, vitamin D binding protein (DBP), profilin, cofilin, depactin, Dnasel, vilin, fragmin, severin, capping protein, β-actinin, acumentin, an actin-sequestering peptide, an actin binding peptide, an actin-mobilizing peptide, an actin polymerization-modulating peptide, or a stimulating agent that stimulates production of an effective amount of said peptide agent in said subject, body, organ, tissue or cell.

DETAILED DESCRIPTION OF THE INVENTION

Without being found to any specific theory, peptide agents as described herein, comprising at least one of Tβ4, an isoform of Tβ4, an N-terminal fragment of Tβ4, a C-terminal fragment of Tβ4, Tβ4 sulfoxide, an LKKTET (SEQ ID NO.: 1) peptide or conservative variant thereof, an LKKTNT (SEQ ID NO.: 2) peptide or conservative variant thereof, a KLKKTET (SEQ ID NO.: 3) peptide or conservative variant thereof, an LKKTETQ (SEQ ID NO.: 4) peptide or conservative variant thereof, Tβ4$^{ala}$, Tβ9, Tβ10, Tβ11, Tβ12, Tβ13, Tβ14, Tβ15, gelsolin, vitamin D binding protein (DBP), profilin, cofilin, depactin, Dnasel, vilin, fragmin, severin, capping protein, β-actinin, acumentin, an actin-sequestering peptide, an actin binding peptide, an actin-mobilizing peptide, an actin polymerization-modulating peptide, promote reversal or prevention of tissue deterioration, injury or damage due to a periodontal disease or disease of oral mucosa, and/or downregulate NF-kappaB or suppress NF-kappaB-mediated action in a body, organ, tissue or cell.

Thymosin beta 4 was initially identified as a protein that is up-regulated during endothelial cell migration and differentiation in vitro. Thymosin beta 4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration, vascularization and wound healing.

In accordance with one embodiment, the invention is a method of treatment for treating, preventing, inhibiting or reducing tissue deterioration, injury or damage due to a periodontal disease or disease of oral mucosa, or for restoring tissue adversely affected by said disease, in a subject, comprising administering to a subject an effective amount of a composition comprising a peptide agent, as described herein.

The invention is applicable to periodontal diseases and diseases of the oral mucosa, including, but limited to, gingivitis and various forms of periodontitis, including aggressive periodontitis, chronic periodontitis, periodontitis as a manifestation of systemic diseases, and necrotizing periodontal diseases.

The present invention also is applicable to downregulating NF-kappaB or suppressing NF-kappaB-mediated action in a body, organ, tissue or cell.

In accordance with one embodiment, the invention is a method of downregulating NF-kappaB or suppressing NF-kappaB-mediated action in a body, organ, tissue or cell comprising administering to a subject an effective amount of a composition comprising a peptide agent as described herein, having NF-kappaB downregulating activity or NF-kappaB-mediated action suppressing activity.

In accordance with one embodiment, the peptide agent is other than Tβ4 and/or other than Tβ4 sulfoxide.

Compositions which may be used in accordance with the present invention include peptide agents such as Thymosin β4 (Tβ4), and/or Tβ4 isoforms, analogues or derivatives, including oxidized Tβ4, N-terminal variants of Tβ4, C-terminal variants of Tβ4, polypeptides or peptide fragments comprising or consisting essentially of the amino acid sequence LKKTET (SEQ ID NO.: 1), LKKTNT (SEQ ID NO.: 2), KLKKTET (SEQ ID NO.: 3), LKKTETQ (SEQ ID NO.: 4), conservative variants thereof, or other peptide agents as described herein, having activity as described herein. International Application Serial No. PCT/US99/17282, incorporated herein by reference, discloses isoforms of Tβ4 which may be useful in accordance with the present invention as well as amino acid sequence LKKTET and conservative variants thereof, which may be utilized with the present invention. International Application Serial No-PCT/GB99/00833 (WO 99/49883), incorporated herein by reference, discloses oxidized Thymosin β4 which may be utilized in accordance with the present invention. Although the present invention is described primarily hereinafter with respect to Tβ4 and Tβ4 isoforms, it is to be understood that the following description is intended to be equally applicable to amino acid sequence LKKTET (SEQ ID NO.: 1), LKKTNT (SEQ ID NO.: 2), KLKKTET (SEQ ID NO.: 3), LKKTETQ (SEQ ID NO.: 4), peptides and fragments comprising or consisting essentially of LKKTET (SEQ ID NO.: 1), LKKTNT (SEQ ID NO.: 2), KLKKTET (SEQ ID NO.: 3), LKKTETQ (SEQ ID NO.: 4), conservative variants thereof having activity as described herein and/or Tβ4 isoforms, analogues or derivatives, including oxidized Tβ4, N-terminal variants of Tβ4, C-terminal variants of Tβ4, or other peptide agents as described herein.

In one embodiment, the invention provides a method of treatment for treating, preventing, inhibiting or reducing tissue deterioration, injury or damage due to a periodontal disease or disease of oral mucosa, or for restoring tissue adversely affected by said disease, in a subject, by contacting the tissue with an effective amount of a composition which contains a peptide agent as described herein. As a non-limiting example, the tissue may be oral mucosa tissue of said subject. The contacting may be directly or systemically. Examples of direct administration include, for example, contacting the tissue, by direct application, injection or infusion, with a solution, mouthwash, toothpaste, lotion, salve, gel, cream, paste, spray, suspension, dispersion, hydrogel, ointment, foam or oil comprising a peptide agent as described herein. Systemic administration includes, for example, intravenous, intraperitoneal, intramuscular or other injections of a composition containing a peptide agent as described herein, in a pharmaceutically acceptable carrier such as water for injection.

The subject preferably is a human or other animal. When the animal is, for example, a dog, the peptide agent may be incorporated into dog food or dog treats such as dog bone treats.

Without being bound to any particular theory, peptide agents in accordance with the present invention may be effective in treating or preventing tissue deterioration, injury or damage do to periodontal disease or disease of oral mucosa by reducing inflammation due to interlukin-8 (IL-8).

In one embodiment, the invention provides a method of downregulating NF-kappaB or suppressing NF-kappaB-mediated action in a body, organ, tissue or cell by contacting the body, organ, tissue or cell with an effective amount of a composition which contains a peptide agent as described herein. As a non-limiting example, the tissue may be spinal tissue of said subject. The contacting may be directly or systemically. Examples of direct administration include, for example, contacting the tissue, by direct application, injection or infusion, with a solution, lotion, salve, gel, cream, paste, spray, suspension, dispersion, hydrogel, ointment, foam or oil comprising a peptide agent as described herein. Systemic administration includes, for example, intravenous, intraperitoneal, intramuscular or other injections of a composition containing a peptide agent as described herein, in a pharmaceutically acceptable carrier such as water for injection. The subject preferably is a human or other animal.

Peptide agents for use in the invention, as described herein, may be administered in any effective amount. For example, a peptide agent as described herein may be administered in dosages within the range of about 0.0001-1,000,000 micrograms, more preferably in amounts within the range of about 0.1-5,000 micrograms, most preferably within the range of about 1-30 micrograms.

In accordance with one embodiment, a peptide agent in accordance with the present invention is administered in a composition at a concentration within a range of 0.00001-1,000 ug/ml, more preferably within ranges of about 0.0001-100 ug/ml, 0.001-10 ug/ml or 0.01-5 ug/ml.

A composition in accordance with the present invention can be administered daily, every other day, every other week, every other month, etc., with a single application or multiple applications per day of administration, such as applications 2, 3, 4 or more times per day of administration.

Many Tβ4 isoforms have been identified and have about 70%, or about 75%, or about 80% or more homology to the known amino acid sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET (SEQ ID NO.: 1) or LKKTNT (SEQ ID NO.: 2), that appears to be involved, inter alia, in mediating actin sequestration or binding. Tβ4 modulates actin polymerization (e.g. β-thymosins appear to depolymerize F-actin by sequestering free G-actin). Tβ4's ability to modulate actin polymerization may be due to its ability to bind to or sequester actin via the LKKTET (SEQ ID NO.: 1) or LKKTNT (SEQ ID NO.: 2) sequence. Thus, as with Tβ4, other proteins which are anti-inflammatory and/or bind or sequester actin, or modulate actin polymerization, including Tβ4 isoforms having the amino acid sequence LKKTET (SEQ ID NO.: 1) or LKKTNT (SEQ ID NO.: 2), may be effective, alone or in a combination with Tβ4, as set forth herein.

Peptide agents as described herein, such as Tβ4 and Tβ4 isoforms including oxidized Tβ4, decrease inflammatory chemokine, cytokine and capase activity.

Thus, it is specifically contemplated that known Tβ4 isoforms, such as Tβ4$^{ala}$, Tβ9, Tβ10, Tβ11, Tβ12, Tβ13, Tβ14 and Tβ15, as well as Tβ4 isoforms not yet identified, will be useful in the methods of the invention. As such Tβ4 isoforms are useful in the methods of the invention, including the methods practiced in a subject. The invention therefore further provides pharmaceutical compositions comprising Tβ4, as well as Tβ4 isoforms Tβ4$^{ala}$, Tβ9, Tβ10, Tβ11, Tβ12, Tβ13, Tβ14 and Tβ15, and a pharmaceutically acceptable carrier.

In addition, other agents or proteins having anti inflammatory activity and/or actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET (SEQ ID NO.: 1) or LKKTNT (SEQ ID NO.: 2), for example, can similarly be employed in the methods of the invention. Such proteins may include gelsolin, vitamin D binding protein (DBP), profilin, cofilin, depactin, Dnasel, vilin, fragmin, severin, capping protein, -actinin and acumentin, for example. As such methods include those practiced in a subject, the invention further provides pharmaceutical compositions comprising gelsolin, vitamin D binding protein (DBP), profilin, cofilin, depactin, Dnasel, vilin, fragmin, severin, capping protein, β-actinin and acumentin as set forth herein.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Tβ4 has been localized to a number of tissue and cell types and thus, agents which stimulate the production of an LKKTET (SEQ ID NO.: 1) or LKKTNT (SEQ ID NO.: 2) peptide such as Tβ4 or another peptide agent as described herein, can be added to or comprise a composition to effect production a peptide agent from a tissue and/or a cell. Such stimulating agents may include members of the family of growth factors, such as insulin-like growth factor (IGF-1), platelet derived growth factor (PDGF), epidermal growth factor (EGF), transforming growth factor beta (TGF-), basic fibroblast growth factor (bFGF), thymosin α1 (Tα1) and vascular endothelial growth factor (VEGF). More preferably, the stimulating agent is transforming growth factor beta (TGF-) or other members of the TGF-superfamily.

In accordance with one embodiment, subjects are treated with a stimulating agent that stimulates production in the subject of a peptide agent as defined herein.

Additionally, other agents that assist in reduction of tissue deterioration, injury or damage due to periodontal disease, or restoring tissue adversely affected by said disease may, or, be administered in conjunction with a peptide agent as described herein. For example, and not by way of limitation, a peptide agent as described herein alone or in combination can be added in combination with any one or more of the following agents: antibiotics, VEGF, KGF, FGF, PDGF, TGF, IGF-1, IGF-2, IL-1, prothymosin α and/or thymosin α1 in an effective amount.

The invention also includes a pharmaceutical or veterinary composition comprising a therapeutically effective amount of a peptide agent as described herein in a pharmaceutically or veterinary acceptable carrier, which may comprise water or another carrier.

In general, the pharmaceutical compositions can be prepared in various forms, such as solutions, suspensions, salves, lotions and the like. In some embodiments, where delivery of a peptidic compound of the invention is to oral tissues, a peptidic compound of the invention may be formulated in a toothpaste, a mouthwash, or may be coated on or embedded in a dental floss or tooth blush. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, anti-pathogenic agents (e.g., antimicrobials, antibacterials, antivirals, antifungals, etc.), antioxidants, chelating agents, and the like.

The actual dosage or reagent, formulation or composition that provides treatment may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

Suitable formulations may include a peptide agent as described herein at a concentration within the range of about 0.001-99% by weight, more preferably within the range of about 0.01-0.1% by weight, most preferably about 0.05% by weight.

The therapeutic approaches described herein involve various routes of administration or delivery of a peptide agent as described herein, including any conventional administration techniques (for example, but not limited to, direct administration, local injection, inhalation, or systemic administration), to a subject. The methods and compositions using or containing a peptide agent as described herein may be formulated into pharmaceutical compositions by admixture with pharmaceutically acceptable non-toxic excipients or carriers.

The peptide agent in accordance with the present invention may be co-administered with other agents which are useful in treating or preventing periodontal disease or disease of oral mucosa. Such other agents may be administered in any suitable effective dosage, such as dosages within in a range of about 0.01-1,000 ng/ml, more preferably within in a range of about 0.1-100 ng/ml, and still more preferably within in a range of about 1-50 ng/ml.

Similarly, the peptide agent in accordance with the present invention may be co-administered with other agents that impact NF-kappaB action. Such other agents may be administered in any suitable effective dosage, such as dosages within in a range of about 0.01-1,000 ng/ml, more preferably within in a range of about 0.1-100 ng/ml, and still more preferably within in a range of about 1-50 ng/ml.

In yet another embodiment, the invention provides a method of treating a subject by administering an effective amount of stimulating agent which modulates gene expression. The term "modulate" refers to inhibition or suppression of expression when a peptide agent as described herein is overexpressed, and induction of expression when a peptide agent as described herein is underexpressed. The term "effective amount" means that amount of stimulating agent which is effective in modulating gene expression of a peptide agent as described herein, resulting in activity as descried herein. A stimulating agent which modulates gene expression of a peptide agent as described herein may be a polynucleotide, for example. The polynucleotide may be an antisense, a triplex agent, or a ribozyme. For example, an antisense directed to the structural gene region or to the promoter region of a peptide agent as described herein may be utilized. The stimulating agent which modulates gene expression of a peptide agent as described herein may also be an RNA molecule.

In another embodiment, the invention provides a method for utilizing compounds that modulate activity of a peptide agent as described herein. Compounds that affect activity of a peptide agent as described herein (e.g., antagonists and agonists) include peptides, peptidomimetics, polypeptides, chemical compounds, minerals such as zincs, and biological agents.

A method for screening for certain stimulating agents as defined herein, comprises contacting a tissue exhibiting periodontal disease or disease of oral mucosa, with a candidate compound; and measuring activity in said tissue of a peptide agent as described herein, wherein an increase of activity of said peptide agent in said tissue, compared to a level of activity of said peptide agent in a corresponding tissue lacking said candidate compound, indicates that said compound is capable of inducing said peptide agent.

A further method for screening for stimulating agents as defined herein, comprises contacting a tissue that exhibits NF-kappaB-mediated action, with a candidate compound; and measuring activity in said tissue of a peptide agent as described herein, wherein an increase of activity of said peptide agent in said tissue, compared to a level of activity of said peptide agent in a corresponding tissue lacking said candidate compound, indicates that said compound is capable of inducing said peptide agent.

Gingivitis is an extremely common inflammatory disease that can cause significant morbidity as it adversely impacts on oral health. Gram negative bacterial adhesion to oral cavity surfaces and subsequent release of endotoxins (LPS) results in the secretion of pro-inflammatory cytokines such as interleukin (IL)-8 by gingival epithelial cells and fibroblasts, and prolonged inflammatory responses can result in severe tissue damage leading to cell death, or apoptosis. Currently available mouthrinses used to control gingivitis are broad spectrum anti-microbials that do not treat the associated inflammatory processes and do not promote the repair of injured oral tissues. Thymosin beta 4 (Tβ4) is a naturally occurring, water-soluble, nontoxic peptide with documented anti-inflammatory, anti-apoptotic and wound healing properties.

Tβ4 has application in an oral health care preparation targeted specifically at counteracting gingival inflammation caused by oral pathogenic bacteria. Tβ4 mouthrinse may be used as an anti-inflammatory adjunct to daily oral health care routines. Tβ4 may suppress gingival tissue inflammatory and apoptotic responses initiated by oral bacteria. Tβ4 may suppress inflammation and apoptosis in gingival cells treated with LPS. Human gingival epithelial cells and fibroblasts are assayed for secretion of IL-8 as a marker of inflammation, and are assayed for apoptosis by monitoring changes in membrane phospholipids. Tβ4 may suppress inflammation by inhibiting IL-8 secretion and may inhibit apoptosis in LPS-challenged cells. The molecular mechanisms by which Tβ4 regulates inflammatory pathways in gingival cells challenged by TNFα or LPS are identified. In gingival epithelial cells and fibroblasts, the activation, phosphorylation, and nuclear translocation of nuclear factor kappa B (NFκB), a central regulator of the inflammatory response, is determined. Tβ4 may inhibit the activation of NFκB and suppress NFκB-regulated gene expression in challenged cells, thus providing evidence for a mechanistic link between Tβ4-regulated inhibition of NFκB and Tβ4-mediated suppression of inflammation.

About 50 percent of the adults in the United States have gingivitis (gum inflammation), 35 percent have some form of periodontitis, and 7 to 15 percent have severe periodontal disease (inflammation of the gums leading to destruction of the bone supporting the teeth). Consequently, the association between periodontal infection and systemic health has important implications for the treatment and management of patients.

Although antimicrobial mouthrinses are available, none contain ingredients that control the tissue inflammation associated with gingivitis. Thymosin beta 4 (Tβ$_4$) is a naturally occurring anti-inflammatory agent that is non-toxic to humans. Tβ$_4$ is a highly stable, water-soluble peptide that could be used in the formulation of a novel non-prescription mouthrinse with combined antimicrobial, anti-inflammatory, and anti-apoptotic properties that would be of high impact with regards to oral health.

Emerging science suggests an association between periodontitis (advanced gum disease) and broader health problems, but a cause and effect relationship has not been established. Listerine® Antiseptic is not indicated to treat periodontitis.

Gingivitis, inflammation of the gingiva or "gums," is an extremely common oral health care concern, with estimates of the percentage of adults with some degree of this inflammatory disease as high as 75%. Left untreated, gingivitis may be a precursor to periodontitis. Gingivitis is preventable and reversible by eliminating the accumulation of plaque. However, poor oral hygiene remains a public health issue, and it has been estimated that 50% of Americans do not see a dentist or dental hygienist regularly due either to fear or lack of insurance. Even in those persons with good oral hygiene, gingivitis can be induced by certain drugs, by viral and fungal infections, by systemic disease such as diabetes; and by hormonal changes that occur during puberty, pregnancy and menopause. Gingivitis not only remains a problem but has the potential to increase as tooth loss from dental caries declines. The need for easily available oral health care products to suppress the development or progression of gingivitis is world-wide and impacts all adults regardless of their state of health.

Brushing, flossing, and the use of mouthrinses are recommended daily regimens to help prevent gingivitis. Currently available over-the-counter rinses use essential oils (Listerine) or cetyl pyridinium chloride (Crest Pro-Health) to kill oral bacteria. Peridex, available by prescription, employs chlorhexidine to destroy bacteria. The currently available mouthrinses are antimicrobials that do not directly address the inflammatory aspect of gingivitis and are not indicated for the more serious inflammatory condition, periodontitis. While it is beneficial to destroy the bacteria that are the underlying cause of plaque formation and gingivitis, the suppression of inflammatory responses initiated by bacteria and their endotoxins as they bind to oral mucosal tissues should also be a goal of oral health care products. Additionally, antimicrobials destroy all oral bacterial species, the potentially beneficial as well as the opportunistic and pathogenic disease-causing ones. Anti-inflammatory agents specifically target cellular responses to the disease-causing bacterial species.

Thymosin beta 4 (Tβ$_4$), a water-soluble, stable, non-toxic peptide, and other peptide agents as described herein, are particularly useful as mouthrinses that combat the inflammatory responses of oral mucosal cells to pathogenic bacteria. The formulation of a mouthrinse with combined antimicrobial and anti-inflammatory properties available over-the-counter will have a direct impact on the oral health of the public.

The invention is further illustrated by the following non-limiting examples.

Example 1

Figure 1:
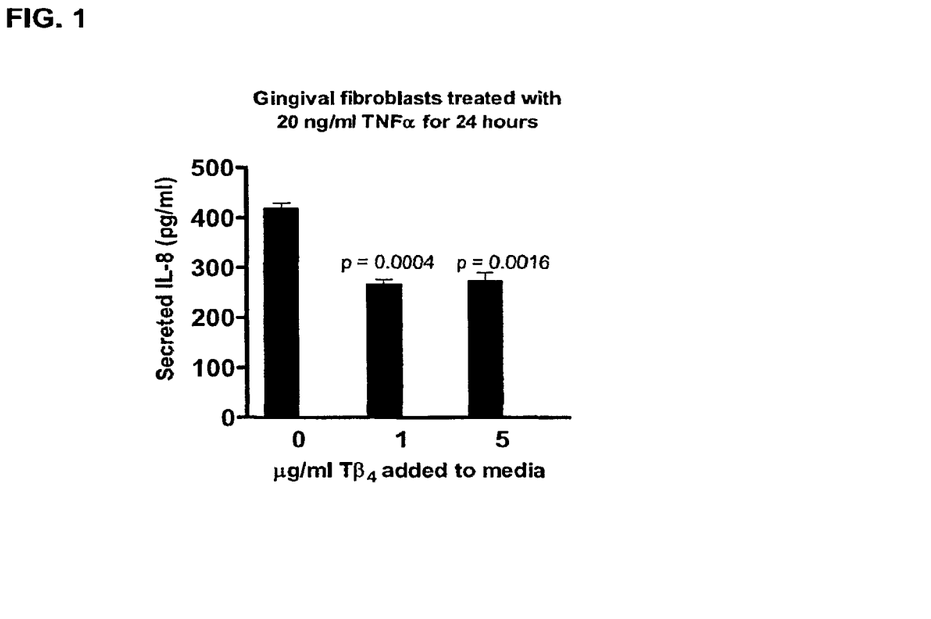
FIG. 1 graphically depicts results achieved with the invention in a first analysis.
Figure 2:
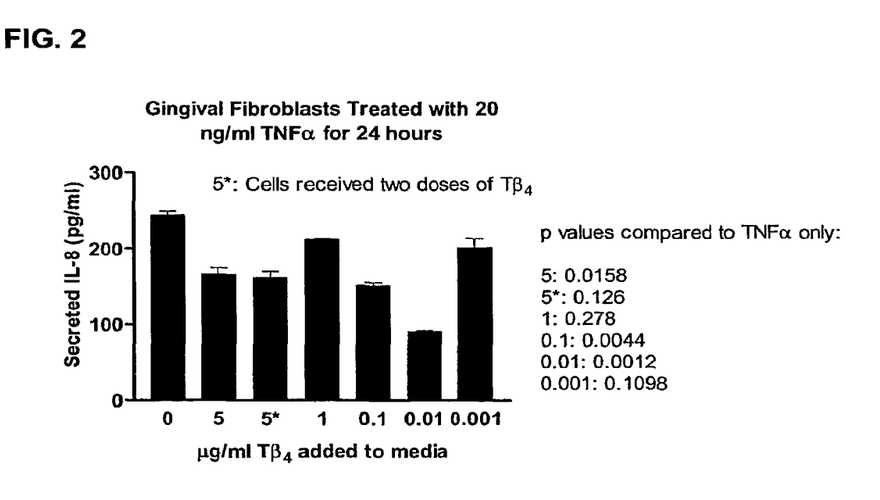
FIG. 2 graphically depicts results obtained with the invention in a second analysis.

Gingival fibroblasts (Fb) were maintained for 24 hours in media only, media plus 20 ng/ml TNF alpha, media plus 20 ng/ml TNF alpha plus 1 ug/ml Tβ4 or media plus 20 ng/ml TNF alpha plus 5 ug/ml Tβ4. As shown in FIG. 1, fibroblasts treated with both levels of Tβ4 showed significantly lower levels of secreted IL-8 (p=0.0004 and p=0.0016 respectively) as compared to fibroblasts not treated with Tβ4.

Example 2

Gingival fibroblasts were treated for 24 hours with 20 ng/ml TNF alpha alone, or in combination with Tβ4 at concentrations ranging from 0.001-5 ug/ml. Fibroblasts treated with all levels of Tβ4 showed lower levels of secreted IL-8, as compared to fibroblasts not treated with Tβ4.

Example 3

Effect of Tβ4 on TNFα-Induced IL-8 Secretion: Dose Response

Human gingival Fb grown to 80% confluence, serum-starved, pretreated with Tb4 for one hour then with 20 ng/ml TNFa±Tb4 for 24 hours. 20 ml of conditioned medium was used for ELISA. After removing medium, cells are fixed, stained, and lysed. OD 550 nm readings are used to normalize ELISA data for total cell number. Media control values were negligible and are not shown.

Figure 3:
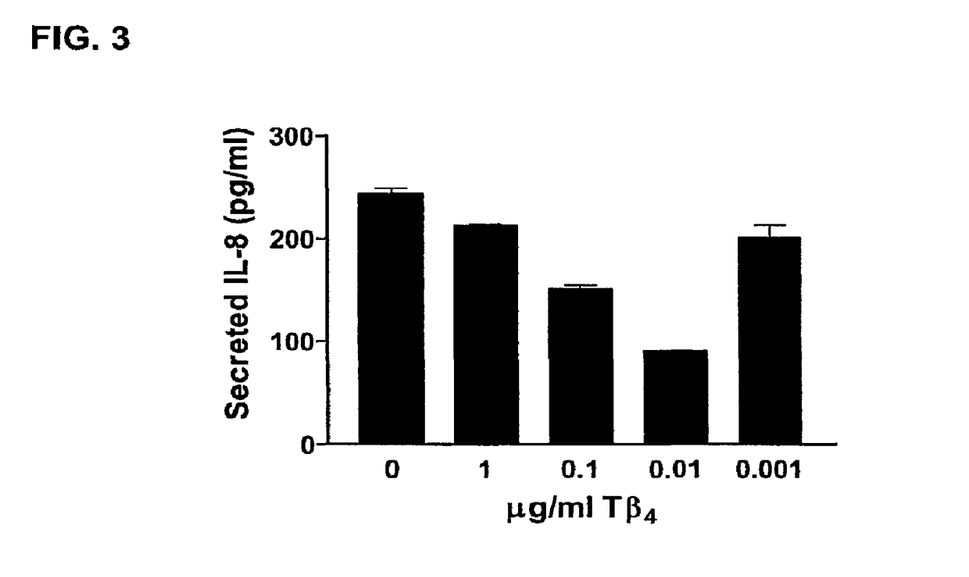
FIG. 3 graphically depicts results obtained with the invention in a third analysis.

Results are shown in FIG. 3, wherein:

0 to 1: p=00278

0 to 0.1: p=0.0044

0 to 0.01: p=0.0012

0 to 0001: p=0.1098

Gingival fibroblasts, a major cellular component of oral tissues, are active participants in the immune response in the oral cavity and secrete cytokines and chemokines such as, IL-8. Fibroblast-derived IL-8 may prolong gingival inflammation and enhance the risk for destruction of gingival connective tissue. Because IL-8 is an important participant in gingival inflammatory processes, we analyzed the efficacy of $T\beta_4$ in modulating IL-8 in an in vitro model of gingival fibroblast inflammation.

Human gingival fibroblasts (HGF-1, ATCC) were stimulated with TNFα (20 ng/ml), a potent pro-inflammatory cytokine widely used in in vitro models of inflammation. Stimulated cells were treated with several concentrations of $T\beta_4$ for 24 hours, and culture supernatants were assayed for IL-8 by ELISA (R&D Systems, Minneapolis, Minn.). Compared to fibroblasts stimulated with TNFα only, simultaneous treatment with $T\beta_4$ inhibited IL-8 secretion in a dose-dependent manner (FIG. 3). Fibroblast treated with 0.01 ug/ml $T\beta_4$ showed the most inhibition of TNFα-stimulated IL-8 secretion (, p=0.0012).

Example 4

Effect of Tβ4 on TNFα-Induced IL-1β Secretion: Dose Response

Human gingival Fb grown to 80% confluence, serum-starved, pretreated with Tb4 for one hour then with 20 ng/ml TNFa±Tb4 for 24 hours. 20 ml of conditioned medium was used for the assay. After removing medium, cells are fixed, stained, and lysed. OD 550 nm readings are used to normalize ELISA data for total cell number. Media control values were negligible and are not shown.

Figure 4:
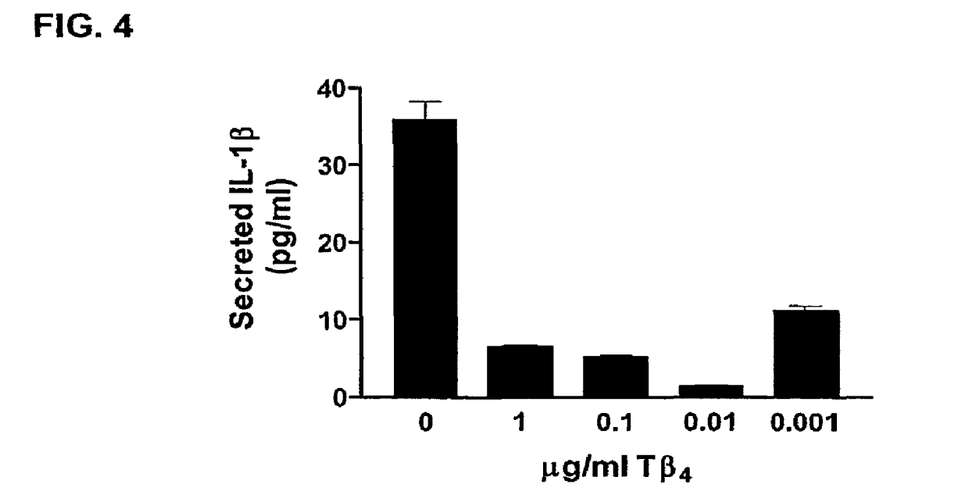
FIG. 4 graphically depicts results obtained with the invention in a fourth analysis.

Results are shown in FIG. 4, wherein:

0 to 1: p=0.0061

0 to 0.1: p=0.0056

0 to 0.01: p=0.0044

0 to 0001: p=0.0091

Example 5

Effect of Tβ4 on TNFα-Induced IL-8 Secretion: Time Course

Human gingival Fb grown to 80% confluence, serum-starved, pretreated with 0.01 mg/ml Tb4 for one hour then with 20 ng/ml TNFa±0.01 mg/ml Tb4 for 4, 8, 12, or 24 hours. 20 ml of conditioned medium was used for the assay. After removing medium, cells are fixed, stained, and lysed. OD 550 nm readings are used to normalize ELISA data for total cell number. Media control values were negligible and are not shown.

Figure 5:
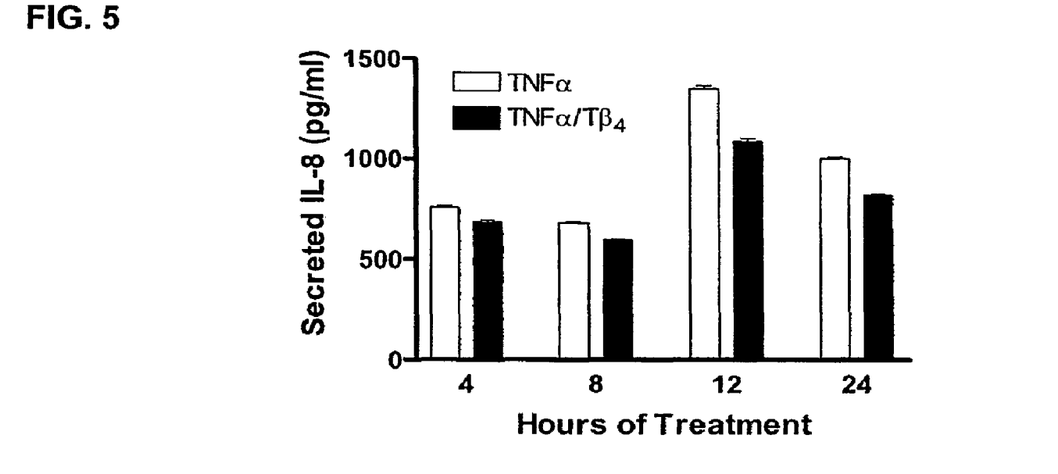
FIG. 5 graphically depicts results obtained with the invention in a fifth analysis.

Results are shown in FIG. 5, wherein:

4 hr: p=0.0454

8 hr: p=0.0086

12 hr: p=0.0080

24 hr: p=0.0033

Example 6

Effect of Tβ4 on TNFα-Induced Apoptosis

Human gingival Fb were serum-starved for 24 hours, pretreated with 0.01 mg/ml Tb4 for 1 hour then stimulated with TNFa±0.01 mg/ml Tb4 for 4 hours. Apoptosis was assayed using the ApoPercentage assay by images and by measuring pixel number.

Figure 6:
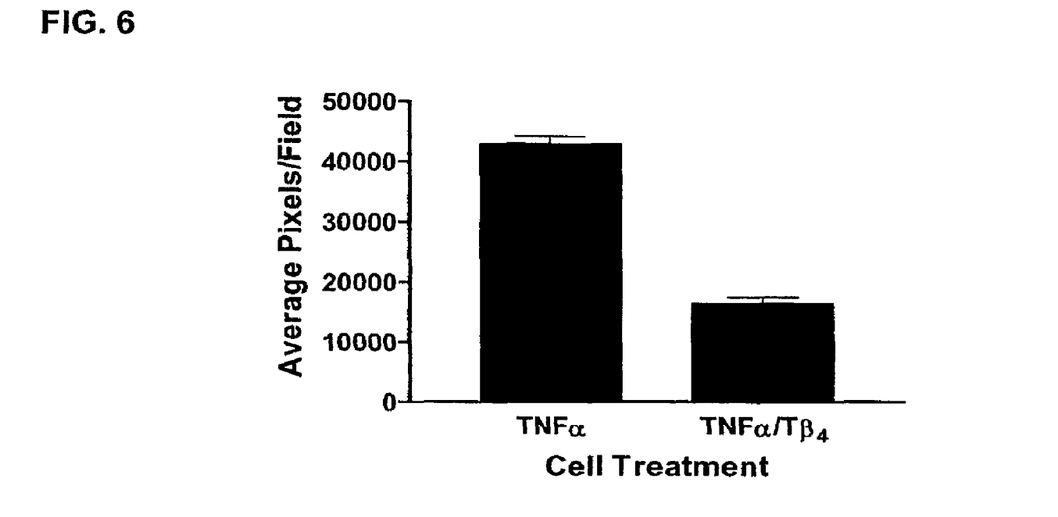
FIG. 6 graphically depicts results obtained with the invention in a sixth analysis.

Results are shown in FIG. 6, wherein

P<0.0001

Example 7

Effect of Tβ4 on Cytotoxicity Induced by Oral Antibacterial Agents

Figure 7A:
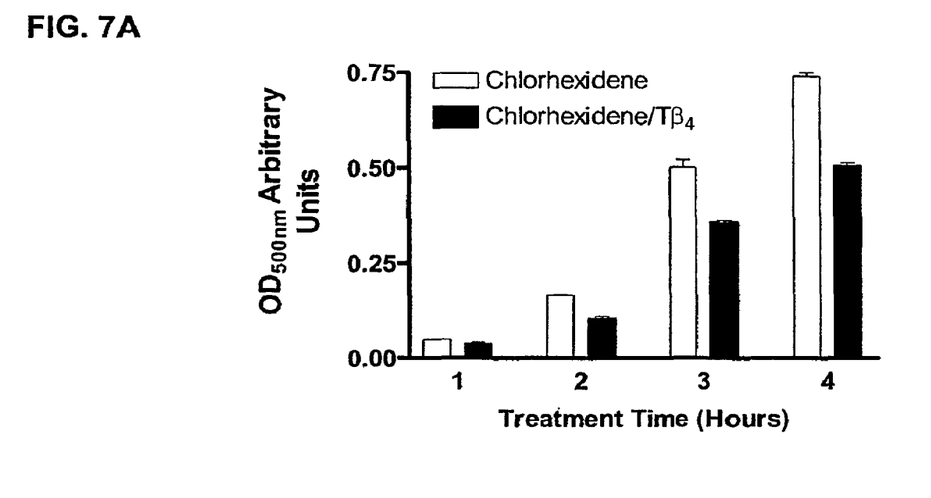
FIGS. 7A-7C graphically depicts results obtained with the invention in a seventh analysis.
Figure 7B:
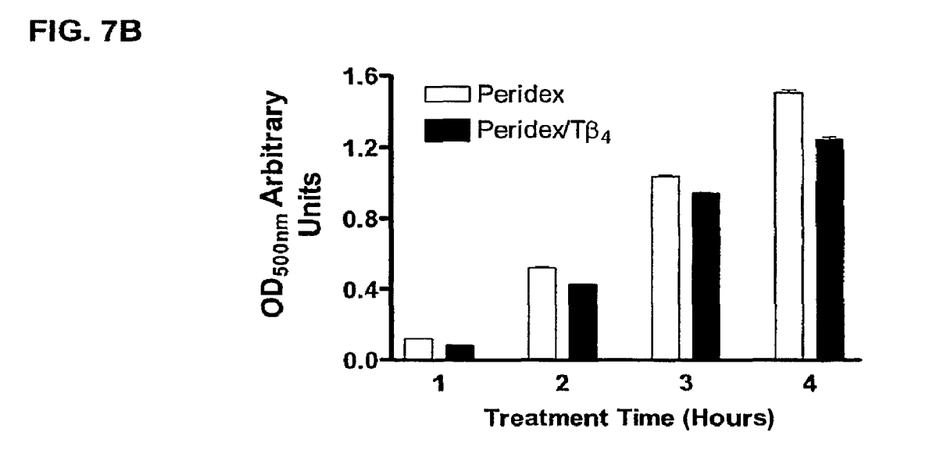
Figure 7C:
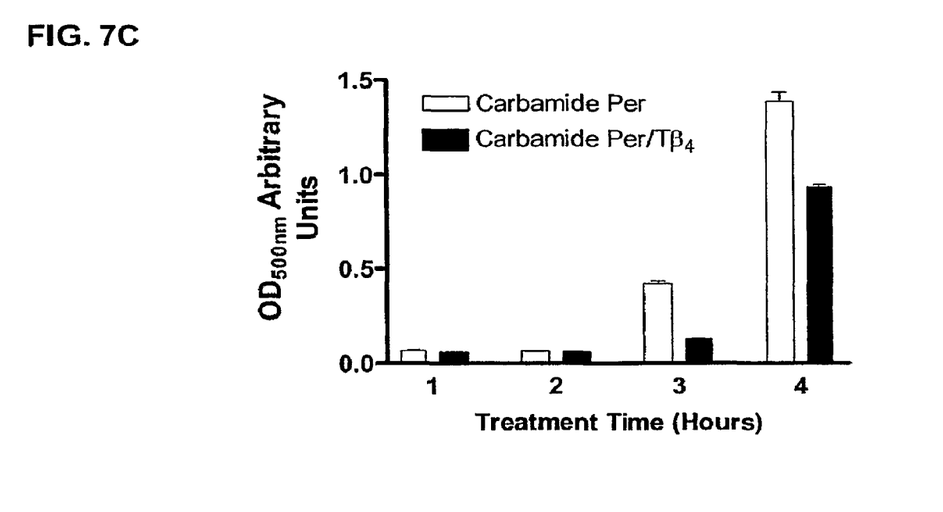

Human gingival Fb grown to 80% confluence. 2 ml 0.002% chlorhexidene, Peridex, or carbamide peroxide±1 mg/ml Tb4 was added to cells for 1, 2, 3, or 4 hours. 100 ml culture medium samples (n=4) were removed at each time point. LDH reagent was added and incubated for 15 minutes. OD readings at 500 nm were taken. FIGS. 7A-7C show the average±SEM.

Results are shown in FIG. 7A, wherein:

CHX 1 hr: p=0.0150

2 hr: p=0.0002

3 hr: p=0.0013

4 hr: p<0.0001

Results are shown in FIG. 7B, wherein:

Peridex 1 hr: p<0.0001

2 hr: p<0.0001

3 hr: p=0.0006

4 hr: p=0.0002

Results are shown in FIG. 7C, wherein:

Carbamide Peroxide 1 hr: p=0.1959

2 hr: p=0.0011

3 hr: p<0.0001

4 hr: p=0.0010

Example 8

Effect of Tβ4 on Apoptosis Induced by Oral Antibacterial Agents

Human gingival Fb were treated with 0.002% chlorhexidene±1 mg/ml Tb4 for 2 hrs. Apoptosis was assayed using the ApoPercentage assay by measuring pixel number.

Figure 8:
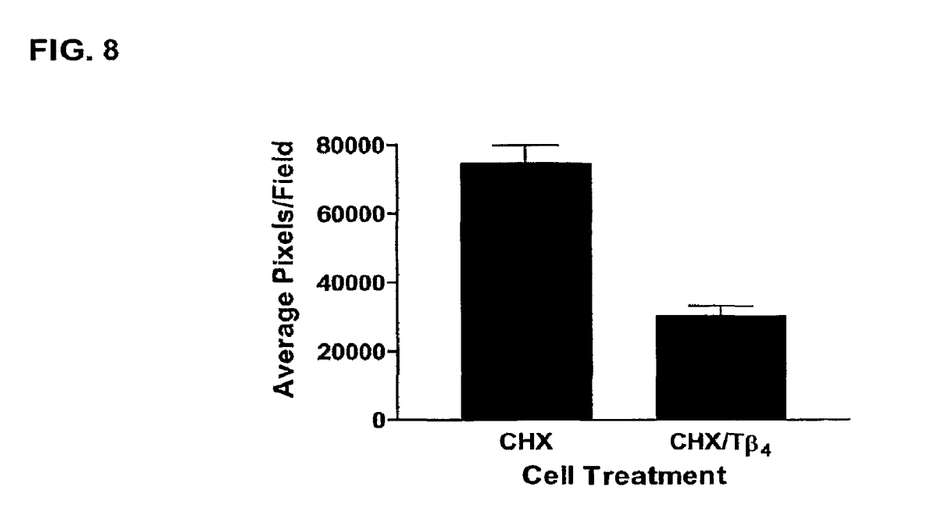
FIG. 8 graphically depicts results obtained with the invention in an eighth analysis.

Results are shown in FIG. 8, wherein

P<0.0001

Example 9

Effect of Tβ4 on LPS-Induced IL-8 Secretion

Human gingival Fb grown to 80% confluence, serum-starved, pretreated with 0.01 mg/ml Tb4 for one hour then with 20 ng/ml TNFa or 10 mg/ml LPS±0.01 mg/ml Tb4 for 4, 8, 12, or 24 hours. 20 ml of conditioned medium was used for the assay. After removing medium, cells are fixed, stained, and lysed. OD 550 nm readings are used to normalize ELISA data for total cell number. Control values were negligible and are not shown.

Figure 9:
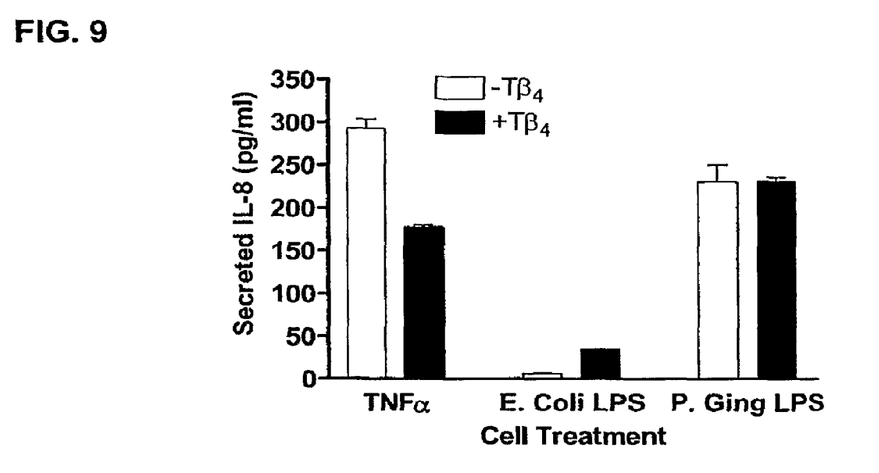
FIG. 9 graphically depicts results obtained with the invention in a ninth analysis.

Results are shown in FIG. 9, wherein:

TNFa to TNFa/Tb4: p=0.0083

Example 10

Tβ$_4$ Inhibits Apoptosis in TNFα Stimulated Gingival Fibroblasts

It is well documented that proteases from oral bacteria such as *P. gingivalis* can induce death in different cell types in vitro, including fibroblasts, epithelial cells, and endothelial cells. Apoptosis can also be induced as a component of the inflammatory response. Using our in vitro model of TNF-α stimulation, we determined the ability of Tβ$_4$ to suppress gingival fibroblast apoptosis. Fibroblasts were stimulated with TNF-α (20 ng/ml) for 8 hours in the presence or absence of 0.01 ug/ml Tβ$_4$.

The fibroblasts were then assayed using the APOPercentage assay (Accurate Chemical, Westbury, N.Y.), which detects changes in cell membrane phospholipids. Apoptotic cells uptake dye, while dye entry does not take place in viable cells. The absorbance of released dye can be measured and correlated to the relative amount of apoptosis in the culture. In gingival fibroblasts Tβ$_4$ significantly inhibits apoptotic cell death induced by TNF-α (p=0.0004). There were a greater number of apoptotic cells in fibroblasts stimulated with TNFα compared to cells stimulated with TNFα and also treated with Tβ4.

Example 11

Thymosin Beta 4 Suppression of Corneal NFκB

Purpose: The purpose of this study was to determine the effect of thymosin beta 4 (Tβ4) on NFκB protein levels, activation, phosphorylation, and nuclear translocation in a model of tumor necrosis factor (TNF)-α-mediated corneal inflammation.

Methods: Transformed (HCET) human corneal epithelial cells were stimulated with the pro-inflammatory cytokine TNF-α and treated with Tβ4. Nuclear NFκB p65 subunit protein levels were assayed using ELISA, and activity was measured by determining NFκB binding to consensus oligonucleotides. NFκB p65 protein phosphorylation was also measured by ELISA. Nuclear translocation of NFκB p65 subunit was assayed by immunofluorescence microscopy.

Results: Tβ4 treatment significantly decreased nuclear NFκB protein levels, NFκB activity and p65 subunit phosphorylation in corneal epithelial cells after TNF-α stimulation. Tβ4 also blocked nuclear translocation of the NFκB p65 subunit in TNF-α-stimulated corneal epithelial cells.

Conclusions: TNF-α initiates cell signaling pathways that converge on the activation of NFκB, thus both are known mediators of the inflammatory process. Tβ4, a protein with diverse cellular functions including wound healing and suppression of inflammation, inhibits the activation of NFκB in TNF-α-stimulated cells. These results have important clinical implications for the role of Tβ4.

The corneal wound repair process is intricately linked to a complex inflammatory response that must be precisely regulated to ensure proper healing and optimal visual outcome. Many studies have contributed information regarding the roles of cytokine and chemokine expression and activity in the post-wound corneal inflammatory response in a wide array of clinical pathologies. For example, in chemically injured corneal epithelial cells, the levels of pro-inflammatory cytokines and chemokines are upregulated. Dry eye induced experimentally in mice, also stimulates production and expression of TNF-α. Additionally corneal epithelial monolayers infected with *Pseudomonas aeruginosa* demonstrated increased expression and secretion of IL-6, IL-8, and TNF-α.

Many studies suggest that TNF-α is a potent pro-inflammatory cytokine considered to be a central mediator of the inflammatory response. It regulates antimicrobial defenses, wound healing, defense against malignancies, and apoptotic cell death. One consequence of the activation of signal transduction pathways subsequent to TNF-α stimulation is the activation of transcription factors necessary for the induction of chemokine gene expression. One major transcription factor is NFκB, formed by the heterodimerization or homodimerization of proteins of the Rel family, the two most important of which are p50 and p65. NFκB mediates diverse biological processes, from inflammation to apoptosis. In unstimulated cells, NFκB dimers are located in the cytoplasm. The family of inhibitory proteins, IκBs, binds to NFκB, masks its nuclear localization signal, and keeps it in the cytoplasm. Various extracellular stimuli, including TNF-α act through different signaling pathways to converge on the activation of IκB kinase (IKK). Phosphorylated IκB is degraded and released from the NFκB dimer, permitting the translocation of NFκB to the nucleus. Nuclear NFκB subsequently binds to κB enhancer elements of target genes. Because of its ability to regulate the expression of inflammatory proteins, NFκB is believed to play a major role in the inflammatory process.

Thymosin beta-4 (Tβ4) is a water-soluble, 43-amino acid acidic polypeptide (pI 5.1) with a molecular weight of 4.9 kDa. Tβ4 is a ubiquitous polypeptide, highly conserved across species, and is found at concentrations of $1 \times 10^{-5}$ to $5.6 \times 10^{-1}$ M in a variety of tissues and cell types. Tβ4 promotes corneal wound healing, decreases inflammation, and modulates the MMP/TIMP balance in a mouse model of corneal alkali injury. Although the mechanism(s) of action of exogenous Tβ4 on corneal wound repair and suppression of inflammation remain unclear, we hypothesize that Tβ4 may interfere with NFκB signaling pathways that are central to the inflammatory response. In this report, we extend our analysis of the interrelationship between Tβ4 and corneal inflammation by providing evidence that Tβ4 suppresses NFκB phosphorylation, activity, and nuclear translocation in cultured human corneal epithelial cells stimulated with TNF-α. Our results indicate that Tβ4 regulates the activity of NFκB.

Materials and Methods

Human Corneal Epithelial Cell Culture

Non-transformed human corneal epithelial cells (HCEC) at passage 3 were purchased from Cascade Biologics (Portland, Oreg.). HCEC were rapidly thawed, seeded onto the appropriate tissue culture plastic substrate, and cultured in serum-free EpiLife medium containing human corneal growth supplement as suggested by Cascade. HCEC were used for experiments at passage 4. The transformed human corneal epithelial cell line 10.014 pRSV-T (HCET) was additionally used in this study. HCET were maintained in serum-free KGM on tissue culture plastic coated with a fibronectin-collagen type I matrix. Cells were cultured in a standard tissue culture incubator at 37° C. and in an atmosphere of 5% $CO_2$ and 95% room air with medium changes every two days.

NFκB Activity Assay

HCET or HCEC at approximately 80% confluence were pre-treated with Tβ4 (1 μg/ml) for 1 hr. Cells were then treated with TNF-α (10 ng/ml, R&D Systems, Minneapolis, Minn.) in the presence or absence of Tβ4 for 5, 15, 30, 45, or 60 minutes. Cells maintained in culture medium only, or Tβ4 only, for 30 minutes were used as controls. At each time point the culture medium was removed and the adherent cells were scraped from the dish into 1 ml of cold PBS. The solution was centrifuged at 3000 rpm for 5 minutes. The cell pellet was lysed in 1 ml of cell extraction buffer provided with the activity assay kit (TransAm NFκB p65 Transcription Factor Assay Kit, Active Motif, Carlsbad, Calif.) on ice for 30 minutes, with vortexing every 10 minutes. The extract was centrifuged at 13,000 rpm for 10 minutes at 4° C. and the supernatant was used for activity assays following the kit protocol. In addition to the activity assay, the ELISA for total NFκB p65 subunit protein was completed simultaneously using aliquots of the same supernatants. ELISA values were used to standardize the activity values to correct for differences in protein concentration in each sample. The assays were repeated three times (n=3) and the results of a representative assay are reported as NFκB activity in arbitrary units±SEM. Statistical analysis was performed using the unpaired Student's t-test with significance set at P<0.05.

NFκB Phosphorylation Assay

HCET were cultured in wells of a 96-well plate until approximately 80% confluent. Cells were pre-treated with Tβ4 (1 μg/ml) for 1 hr. Cells were then treated with TNF-α (10 ng/ml) in the presence or absence of Tβ4 for 5, 15, 30, 45, or 60 minutes. Cells maintained in culture medium only, or Tβ4 only, for 30 minutes were used as controls. At each time point adherent cells were fixed in cell fixing buffer containing 4% glutaraldehyde according to the phosphorylation assay kit protocol (CASE, cellular activation of signaling ELISA for phosphoserine 276 of NFκB p65 subunit, SuperArray, Frederick, Md.). Fixed cells were then processed using phospho-specific (phosphoserine 276 p65) or pan-protein specific (nonphosphorylated p65) primary antibodies and HRP-conjugated secondary antibodies. Following incubation with developing and stop solutions provided with the kit, individual well absorbance was read at 450 nm. Variation in cell number in individual wells was corrected by assaying the OD 540 nm of stained cells following completion of the phosphorylation assay and performing numerical correction of the OD 450 nm values. The assay was repeated twice (n=8) and a representative result is presented as relative amounts of phosphorylated and nonphosphorylated NFκB in arbitrary units±SEM. Statistical analysis was performed using the unpaired Student's t-test with significance set at P<0.05.

NFκB Protein Levels

HCET were cultured until approximately 80% confluent. Cells were pre-treated with Tβ4 (1 μg/ml) for 1 hr. Cells were then treated with TNF-α (10 ng/ml) in the presence or absence of Tβ4 for various times. Cells maintained in culture medium only, or Tβ4 only were used as controls. The culture medium was removed and the adherent cells were scraped from the dish into 1 ml of cold PBS. The solution was centrifuged at 3000 rpm for 5 minutes. The cell pellet was resuspended in 0.5 ml hypotonic buffer (20 mM Tris-HCl, pH 7.4, 10 mM NaCl, 3 mM $MgCl_2$) and incubated on ice for 15 minutes. 25 μl of 10% NP-40 was added with vortexing. The homogenate was centrifuged for 10 minutes at 3000 rpm at 4° C. The pellet was resuspended in 100 μl of the cell extraction buffer and incubated for 30 minutes on ice with vortexing every 10 minutes. The homogenate was centrifuged at 14,000 rpm for 30 minutes at 4° C. The resulting supernatant was used for the NFκB total p65 subunit ELISA. A representative analysis is presented as NFκB protein (pg/ml)±SEM. Statistical analysis was performed using the unpaired Student's t-test with significance set at P<0.05.

Nuclear Translocation of NFκB

HCET were cultured on collagen-coated 4 chambered glass microscope slides to approximately 80% confluence. Cells were pre-treated with Tβ4 (1 μg/ml) for 1 hr. Cells were then treated with TNF-α (10 ng/ml) in the presence or absence of Tβ4 for 30 minutes. Cells maintained in culture medium only, or Tβ4 only were used as controls. Cells were fixed in 3.7% glutaraldehyde/PBS for 10 minutes then washed in PBS. Cells were permeabilized in 1% Triton X-100 for 5 minutes and washed again. The cells were then incubated with rabbit polyclonal antibodies specific for the N-terminus of human p65 NFκB (Santa Cruz Biotechnologies, Santa Cruz, Calif.) followed by FITC-conjugated goat anti-rabbit secondary antibodies. Digitized images were captured and stored (Axiophot fluorescence microscopy and imaging system, Carl Zeiss Medicine, Inc., Thornwood, N.Y.).

Results

NFκB Activity in Human Corneal Epithelial Cells

We hypothesized that Tβ4 functions as a transcription factor mediator in addition to its other known cellular functions. To provide support for this hypothesis, we examined the effect of Tβ4 on the activity of NFκB in human corneal epithelial cells stimulated with TNF-α in vitro. Cultured cells were employed for these studies because sufficient material for detailed biochemical analyses could be easily generated. Transcription factor activity was analyzed calorimetrically using an assay that measured the ability of NFκB to bind to oligonucleotides containing consensus κB binding motifs immobilized to a plastic substrate. Whole-cell lysates were used for these analyses per protocol since activated NFκB is presumed to be located only within the nucleus.

Figure 10:
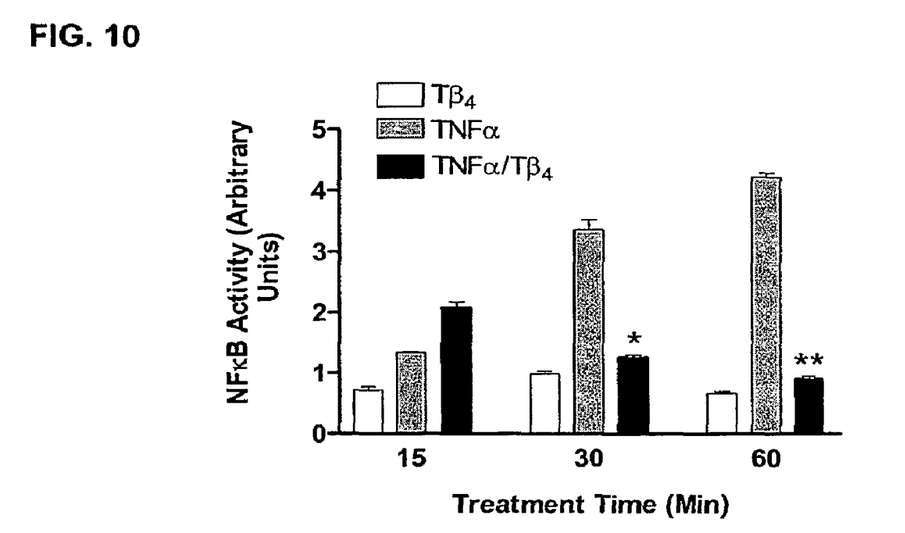
FIG. 10 graphically depicts results obtained with the invention in a tenth analysis.

In the transformed human corneal epithelial cell line HCET, treatment of cells with TNF-α resulted in a progressively increased level of NFκB activity commensurate with time of stimulation (FIG. 10). The treatment of TNF-α stimulated cells with Tβ4 resulted in increased NFκB activity at 5, 10 (results not shown), 15 (FIG. 10), and 20 (results not shown) minutes of stimulation compared to cells stimulated with TNF-α. However, at 30 and 60 minutes, Tβ4 treatment significantly suppressed TNF-α induced activation of NFκB, and activity approached that of cells treated with Tβ4 alone.

Although transformed cell lines provide ample material for analyses, experimental results can be of concern since it is not clearly known how the cells may differ from in vivo counterparts. To complement NFκB activity assays in transformed human corneal epithelial cells, we also performed analyses in non-transformed human corneal epithelial culture and found similar results of decreased NFκB activity with Tβ4 treatment after TNF-α stimulation (results not shown). Based on these results, we were confident that the transformed line, HCET, could be used for further analysis of NFκB dynamics in Tβ4-treated, and TNF-α-stimulated, conditions.

Effect of Tβ4 on NFκB Phosphorylation

Figure 11:
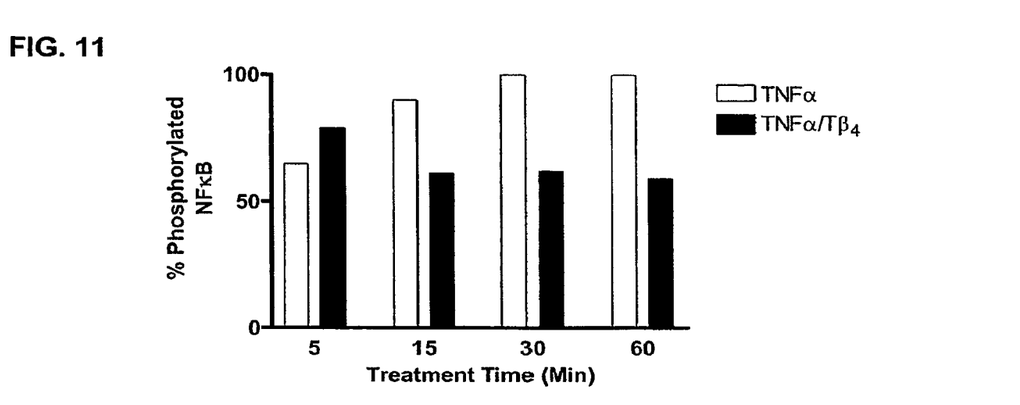
FIG. 11 graphically depicts results obtained with the invention in an eleventh analysis.

In addition to nuclear translocation, the p65 subunit of NFκB must undergo phosphorylation on several serine residues in order to be activated. It has been reported that serine 276 is the major phosphorylation site of p65 and its phosphorylation is essential for p65-dependent cellular responses. Since our studies suggested that Tβ4 could suppress inflammatory mediator induced NFκB activation, we next determined the ability of Tβ4 to regulate the phosphorylation of the serine 276 residue of the p65 subunit of NFκB. We used an ELISA approach that allowed for the measurement of phosphorylated and nonphosphorylated NFκB levels on groups of identically treated cells. Commensurate with increased NFκB activity in corneal epithelial cells treated with TNF-α, we observed an increase in the relative percentage of cellular NFκB that was phosphorylated (FIG. 11). By 30 minutes of TNF-α stimulation, essentially all of the NFκB was phosphorylated. Treatment of TNF-α-stimulated corneal epithelial cells with Tβ4 reduced NFκB phosphorylation levels by 45%.

Figure 12:
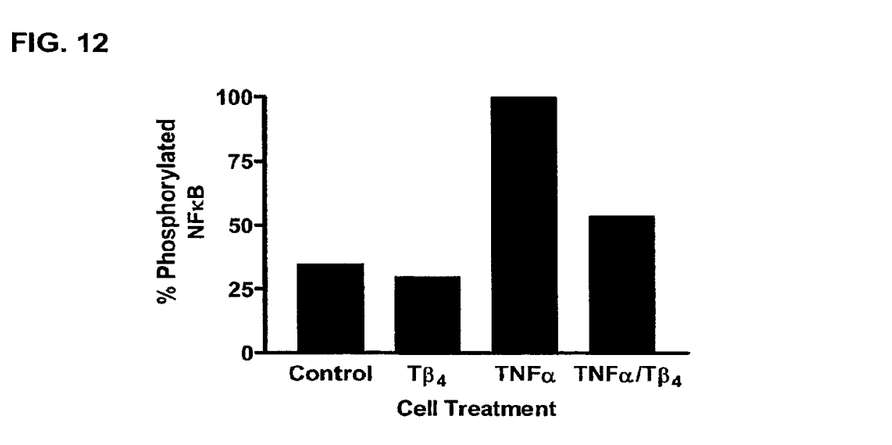
FIG. 12 graphically depicts results obtained with the invention in a twelfth analysis.

We focused on an analysis of phosphorylation levels at 30 minutes of TNF-α stimulation because our studies as shown in FIG. 10 revealed that Tβ4 could significantly suppress NFκB activity at this time point. In media control cells and in cells treated with Tβ4 only, levels of nonphosphorylated NFκB were significantly higher than levels of phosphorylated NFκB (FIG. 12). Conversely, in cells stimulated with TNF-α for 30 minutes essentially all of the NFκB was in the phosphorylated form. In contrast, in cells that were treated with Tβ4 during TNF-α stimulation, the levels of phosphorylated NFκB were significantly decreased. The presence of Tβ4 during TNF-α stimulation reduced the proportion of phosphorylated NFκB from 100% to 55%.

Effect of Tβ4 on NFκB Nuclear Translocation

Figure 13:
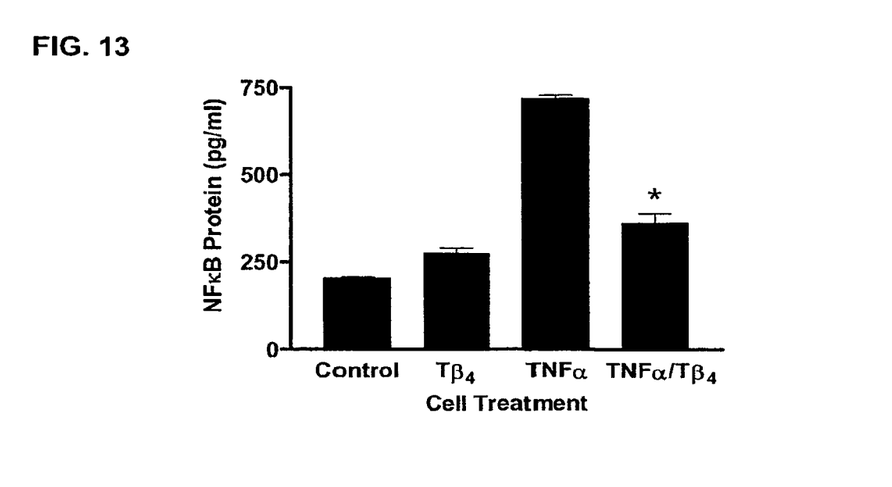
FIG. 13 graphically depicts results obtained with the invention in a thirteenth analysis.

Nuclear translocation is an essential downstream event in NFκB mediated gene transcription. Inhibition of nuclear translocation by Tβ4 would provide additional support to demonstrate that this molecule plays a role in the regulation of NFκB inflammatory processes. HCET were treated for 30 minutes and the amount of NFκB protein in nuclear fractions was measured by ELISA. Only activated, phosphorylated NFκB is capable of translocating to the nucleus. Compared to media control cells or cells treated with Tβ4 only, the amount of NFκB protein measured in the nuclear fraction of cells treated with TNF-α was significantly increased (FIG. 13). However, treatment of cells with Tβ4 during TNF-α activation resulted in significant decrease of measurable NFκB protein in nuclear fractions. This suggests that Tβ4 suppressed nuclear translocation of NFκB under conditions of TNF-α stimulation.

The nuclear translocation of NFκB was also examined morphologically in HCET by immunofluoresence microscopy using an antibody specific for the p65 subunit. In both media control cells and cells treated with Tβ4 only NFκB p65 protein was localized to the cytoplasm. In cells treated with TNF-α only NFκB showed a predominantly nuclear localization, indicating its translocation in response to TNF-α signaling. In cells treated with Tβ4 during the period of TNF-α stimulation the fluorescence pattern appeared to be mainly perinuclear, although evidence of both cytoplasmic and nuclear NFκB localization could be observed.

CONCLUSIONS

Tβ4 suppresses NFκB activation after pro-inflammatory stimulation. In human corneal epithelial cells (both primary and transformed), TNF-α-induced NFκB activation is rapid and sustained. NFκB-induced gene expression requires that NFκB not only becomes activated, but it must also be phosphorylated and must physically translocate from cytoplasm to the nucleus Tβ4 treatment inhibits all three of these central events.

Suppression of TNF-α-induced NFκB activation is not immediate as maximal effects of Tβ4 were time related. Although Tβ4 is intracellular, following microinjection into intact cells, fluorescently labeled Tβ4 has both a diffuse cytoplasmic and a pronounced nuclear staining. Since Tβ4 can also assume a nuclear localization it is interesting to speculate that the time-related inhibition of NFκB activation may represent Tβ4 blocking the cyclic reentry of activated NFκB into the nucleus. We cannot discount the possibility however that Tβ4 inhibits events upstream of NFκB nuclear translocation, including the phosphorylation and activation of IκB kinase.

Figure Legends

FIG. 10. Tβ4 suppresses NFκB activity in human corneal epithelial cells in vitro. Transformed human corneal epithelial cells (HCET) were treated with Tβ4 only (open bars) or stimulated with TNF-α (gray bars) only. HCET were also stimulated with TNF-α and simultaneously treated with Tβ4 (black bars) for the times indicated. At assay times less than 20 minutes, Tβ4 treatment resulted in increased NFκB activity in TNF-α stimulated cells (only the 15 minutes data is shown). In contrast by 30 minutes of Tβ4 treatment, NFκB activity was significantly suppressed in TNF-α stimulated cells (*P=0.0068, **P<0.0001). Note that NFκB activity in HCET treated with Tβ4 alone is consistently lower than in cells treated with TNF-α. NFκB activity in media control cells was negligible and is not shown.

FIG. 11. Tβ4 suppresses NFκB phosphorylation in human corneal epithelial cells in vitro. HCET were stimulated with TNF-α in the presence or absence of Tβ4 for the times indicated. Using an ELISA approach, relative levels of phosphorylated (serine 279 of p65) and nonphosphorylated NFκB were measured. In cells stimulated with TNF-α essentially all of the NFκB p65 is phosphorylated by 30 minutes. Treatment of TNF-α stimulated cells with Tβ4 inhibits the phosphorylation of NFκB by 45%.

FIG. 12. Tβ4 suppresses NFκB phosphorylation in human corneal epithelial cells in vitro. HCET were treated for 30 minutes as indicated. Using an ELISA approach, relative levels of phosphorylated (serine 279 of p65) and nonphosphorylated NFκB were measured. In media control cells and in cells treated with Tβ4 only, most of the NFκB exists in the nonphosphorylated form. In contrast, in cells stimulated with TNF-α essentially all of the NFκB p65 is phosphorylated. Treatment of TNF-α stimulated cells with Tβ4 inhibits the phosphorylation of NFκB by 45%.

FIG. 13. Tβ4 suppresses NFκB nuclear translocation in human corneal epithelial cells in vitro. HCET were treated for 30 minutes as indicated. Using an ELISA approach, the relative levels of NFκB in the nuclear fractions of cell lysates were measured. Note the significant increase in nuclear NFκB protein in cells treated with TNF-α only compared to media control cells or cells treated with Tβ4 only. Treatment of TNF-α stimulated cells with Tβ4 significantly reduces the level of nuclear NFκB protein (*P=0.0066).

The invention claimed is:

1. A method of downregulating NF-kappaB or suppressing NF-kappaB-mediated action in a spinal tissue of a subject in need thereof, comprising administering to said spinal tissue of said subject an effective amount of a composition comprising a peptide agent comprising at least one of Thymosin beta 4 (Tβ4), an isoform of Tβ4, an N-terminal fragment of Tβ4, a C-terminal fragment of Tβ4, Tβ4 sulfoxide, an LKKTET (SEQ ID NO.: 1) peptide or conservative variant thereof, an LKKTNT (SEQ ID NO.: 2) peptide or conservative variant thereof, a KLKKTET (SEQ ID NO.: 3) peptide or conservative variant thereof, and an LKKTETQ (SEQ ID NO.: 4) peptide or conservative variant thereof, in said spinal tissue, so as to downregulate NF-kappaB or suppress NF-kappaB-mediated action in said spinal tissue.

2. The method of claim 1 wherein said peptide agent comprises thymosin beta 4 (Tβ4).

3. The method of claim 1 wherein said peptide agent comprises LKKTET (SEQ ID NO.: 1) or LKKTNT (SEQ ID NO.: 2).

4. The method of claim 1 wherein said peptide agent comprises amino acid sequence KLKKTET (SEQ ID NO.: 3), amino acid sequence LKKTETQ (SEQ ID NO.: 4), and N-terminal variant of Tβ4, a C-terminal variant of Tβ4, or an isoform of Tβ4.

5. The method of claim 1 wherein said peptide agent is administered to said spinal tissue at a dosage within a range of about 1-30 micrograms.

6. The method of claim 1 wherein said peptide agent is administered by direct administration to said spinal tissue, or by injection, or by intravenous, intraperitoneal, intramuscular, subcutaneous, transdermal or oral administration, to said subject.

7. The method of claim 1 wherein said peptide agent is administered systemically.

8. The method of claim 1 wherein said peptide agent is administered directly.

9. The method of claim 1 wherein said composition is in a form of a solution, gel, cream, paste, lotion, spray, suspension, dispersion, salve, hydrogel, ointment, foam or oil.

10. The method of claim 1 wherein said peptide agent is a recombinant or synthetic peptide.

* * * * *

SEQUENCE LISTING

<160> NUMBER OF SEQ ID NOS: 4

<210> SEQ ID NO 1
<211> LENGTH: 6
<212> TYPE: PRT

```
<213> ORGANISM: Homo sapiens

<400> SEQUENCE: 1

Leu Lys Lys Thr Glu Thr
1               5

<210> SEQ ID NO 2
<211> LENGTH: 6
<212> TYPE: PRT
<213> ORGANISM: Homo sapiens

<400> SEQUENCE: 2

Leu Lys Lys Thr Asn Thr
1               5

<210> SEQ ID NO 3
<211> LENGTH: 7
<212> TYPE: PRT
<213> ORGANISM: Homo sapiens

<400> SEQUENCE: 3

Lys Leu Lys Lys Thr Glu Thr
1               5

<210> SEQ ID NO 4
<211> LENGTH: 7
<212> TYPE: PRT
<213> ORGANISM: Homo sapiens

<400> SEQUENCE: 4

Leu Lys Lys Thr Glu Thr Gln
1               5
```